United States Patent [19]
Bogart

[11] Patent Number: 5,512,041
[45] Date of Patent: Apr. 30, 1996

[54] WOUND DRESSING FOR PROMOTING MOIST WOUND HEALING

[75] Inventor: Larry Bogart, Penn Valley, Pa.

[73] Assignee: Scott Health Care, Philadelphia, Pa.

[21] Appl. No.: 319,785

[22] Filed: Oct. 7, 1994

[51] Int. Cl.⁶ ..................................... A61F 13/00
[52] U.S. Cl. ............................. 602/58; 602/56; 604/307; 604/336; 428/40
[58] Field of Search .................................... 602/42, 43, 45, 602/52, 54, 56, 57, 58; 664/304, 307; 428/40, 317.3, 317.5

[56] References Cited

U.S. PATENT DOCUMENTS

| | | | |
|---|---|---|---|
| 2,823,672 | 2/1958 | Schladermundt et al. | 602/57 |
| 2,905,174 | 9/1959 | Smith | 602/42 |
| 3,416,522 | 12/1968 | Yeremian | 604/304 |
| 3,416,525 | 12/1968 | Yeremian | 604/304 |
| 3,416,526 | 12/1968 | Yeremian | 604/304 |
| 3,645,835 | 2/1972 | Hodgson . | |
| 3,870,041 | 3/1975 | Davies . | |
| 4,499,896 | 2/1985 | Heinecke . | |
| 4,561,435 | 12/1985 | McKnight et al. . | |
| 4,649,909 | 3/1987 | Thompson . | |
| 4,657,006 | 4/1987 | Rawlings et al. . | |
| 4,706,662 | 11/1987 | Thompson | 128/155 |
| 4,753,230 | 6/1988 | Carus et al. | 128/156 |
| 4,753,231 | 6/1988 | Lang et al. . | |
| 4,807,613 | 2/1989 | Koehnke et al. | 602/57 |
| 4,901,714 | 2/1990 | Jensen | 128/156 |
| 4,925,453 | 5/1990 | Kannankeril | 604/378 |
| 5,061,258 | 10/1991 | Martz | 604/307 |
| 5,147,698 | 9/1992 | Cole | 602/54 |
| 5,158,555 | 10/1992 | Porzilli | 604/304 |
| 5,250,043 | 10/1993 | Castellana et al. | 604/336 |

FOREIGN PATENT DOCUMENTS 816012  8/1959  United Kingdom .

Primary Examiner—Randall L. Green
Assistant Examiner—Chalin Smith
Attorney, Agent, or Firm—Burns, Doane, Swecker & Mathis

[57] ABSTRACT

A wound dressing for promoting moist wound healing comprising a backing sheet coated with a pressure-sensitive adhesive, an absorbent pad adhered to the adhesive, and a net extending across the pad and adhered to the adhesive. The perimeter of the pad is completely surrounded by a portion of the adhesive. The backing sheet comprises a strip of stretchable, liquid-permeable, non-woven fabric and a semi-occlusive film. The fabric strip is preferably disposed on an interior side of the film and carries the adhesive. The film defines an external face of the dressing and covers the entire surface area of the fabric strip.

17 Claims, 3 Drawing Sheets

WOUND DRESSING FOR PROMOTING MOIST WOUND HEALING

BACKGROUND OF THE INVENTION

The present invention relates to wound dressings of the type which prevent a wound from drying out in order to promote moist wound healing.

The fluid produced by the human body and which accumulates in a wound is commonly referred to as "wound exudate". Wound exudate comprises a mixture of substances including water, salts, proteins, and bacteria. Various studies have demonstrated that, if kept moist, wounds tend to heal faster, especially in the final stages of healing. That form of healing is called "moist wound healing".

Traditional dressings prevented the escape of moisture (water) in liquid form, but the moisture tended to escape in vapor form at a rate which caused the wound to dry out too rapidly for moist wound healing to occur. Therefore, dressings have been designed to minimize the escape of moisture vapor as well as moisture liquid.

For example, a dressing 1 depicted in FIG. 5 comprises a backing sheet 2 coated with an adhesive layer, an absorbent pad 4, one side of the pad being adhered to the adhesive, and the other side carrying a liquid permeable net 5. The backing sheet is formed of a semi-occlusive, liquid and bacteria impermeable, polyurethane film. Once the dressing has been applied to a patient's skin S, the escape of moisture liquid is prevented, whereas moisture vapor can escape through the film 2 as demonstrated by arrows 6 and 7. The rate of that escape is controlled by the amount of resistance offered by the adhesive layer (not shown) and the semi-occlusive film 2. The rate of moisture escape, i.e., the so-called moisture vapor transmission rate (MVTR) of the dressing, is a function of a number of factors, such as the type and thickness of the adhesive layer, and the type and thickness of semi-occlusive film which is used. The MVTR characteristic of the dressing represents a rate of moisture transmission per unit area of the dressing for 24 hr., so the overall moisture loss per day of the dressing can be determined by multiplying the MVTR by the size of the area through which vapor can escape.

The above-described dressing 1 effectively controls the rate of vapor escape, since all of the escaping vapor must pass through the semi-occlusive film 2. However, the dressing suffers from certain drawbacks, most notable of which is a considerable difficulty in handling the dressing during application. That is, the film 2 is exceedingly thin and flexible and frequently becomes doubled up and stuck to itself, whereupon it becomes useless. Many of those types of dressings become ruined in the process of being applied and must be discarded.

Another conventional type of dressing 10, depicted in FIG. 6, avoids the above-described handling problem. That dressing 10 comprises a backing sheet 12 formed of a stretchable, liquid permeable fabric, an absorbent pad 14 adhered to an adhesive layer covering one side of the backing sheet 12, and a liquid permeable net 18 disposed over the pad 14. The stretchable fabric 12 is easier to handle than the film 2 of the dressing depicted in FIG. 5, thus making it less likely that the dressing will be ruined in the process of being applied. In order to resist the escape of moisture vapor, a semi-occlusive (i.e., vapor permeable, bacteria and liquid impermeable) polyurethane film 28 extends through the center of the pad 14. Some moisture vapor escapes through the film 28 (see arrow 6A), so its rate of escape is controlled by the film. However, moisture vapor is also able to bypass the film 28 (see arrow 7A) and thus escapes in an essentially uncontrolled manner. Consequently, the MVTR of the dressing is only partially determined by the adhesive-coated semi-occlusive film. The MVTR of the dressing 10 is not that of the adhesive-coated film 12, but is greater, due to the ability of moisture vapor to bypass the film and escape at a faster rate than the moisture vapor passing through the film. This means that different sized dressings designed according to FIG. 6 will not have the same MVTR because as the dressing size decreases, the size of the vapor escape area surrounding the periphery of the pad 14 represents a greater percentage of the overall vapor escape area of the dressing. Consequently, the MVTR varies inversely with the size of the dressing.

Therefore, it would be desirable to provide a dressing which exhibits a uniform MVTR from one size to the next and yet which is easier to handle than the dressing shown in FIG. 5.

Another area of concern in connection with wound dressings relates to the leakage of wound exudate. Two major causes or leakage are shearing (rubbing) forces applied to the dressing, resulting in premature removal of the dressing from the wound, and saturation of the pad with wound exudate resulting in leakage from the edges of the dressing. Leakage of wound exudate is of concern, because such leakage can expose others to infection and require that bed clothing be laundered more frequently.

Therefore, an important characteristic of the dressing is its ability to stay on the patient when rubbed against bed sheets. The main physical characteristics which will determine a dressing's ability to stay on is the strength of adhesion to the skin and the shear forces generated as the dressing is rubbed against the surface. A high (strong) adhesion will ensure that the dressing stays in place, but it will likely cause discomfort or damage to the skin when the dressing is removed. A way to enable the adhesive strength to be reduced is to decrease the friction forces which must be resisted by the adhesive. That is done by lowering the coefficient of friction of the dressing's external surface. Plastic film dressing can have lower frictional coefficients than non-woven fabrics, so the dressing according to FIG. 6 has a greater coefficient of friction than the dressing according to FIG. 5 and will generate higher shear forces when rubbed against a surface.

Therefore, it would be desirable to provide a wound dressing which not only has a uniform MVTR from one size to the next and is easy to handle, but which also tends to minimize the generation of shearing forces.

SUMMARY OF THE INVENTION

The present invention relates to a wound dressing for promoting moist wound healing. The dressing comprises a backing sheet, and an absorbent pad. The backing sheet is formed of multiple, permanently attached layers and contains on one side thereof a pressure sensitive adhesive. One of the layers comprises a stretchable strip of vapor permeable, non-woven fabric. Another of the layers comprises a semi-occlusive film. The strip and the film have coextensive outer perimeters. The absorbent pad is mounted on the backing sheet by being affixed to the adhesive layer, with an outer perimeter of the pad being spaced inwardly from the entire outer perimeter of the backing sheet.

Preferably, a liquid permeable net overlies the pad and includes an outer portion affixed to the adhesive. An outer perimeter of the net is completely surrounded by a portion of the backing sheet which defines a skin-attachment portion of the dressing. The net defines a wound-contacting portion of the dressing.

The film is preferably disposed externally of the strip to define an exterior face of the dressing and exhibits a low coefficient of friction.

BRIEF DESCRIPTION OF THE DRAWINGS

The objects and advantages of the invention will become apparent from the following detailed description of a preferred embodiment thereof in connection with the accompanying drawings in which like numerals designate like elements and in which.

DETAILED DESCRIPTION OF A PREFERRED EMBODIMENT OF THE INVENTION

A wound dressing 50 depicted in FIGS. 1–4 comprises a multi-layer (more than one), rectangular backing sheet 51 formed by a stretchable strip 52 and a semi-occlusive film 54. The strip 52 comprises any suitable stretchable, non-woven fabric which is vapor-permeable (or even liquid permeable), e.g., a blend of polyester, wood pulp, and rayon.

Figure 4:
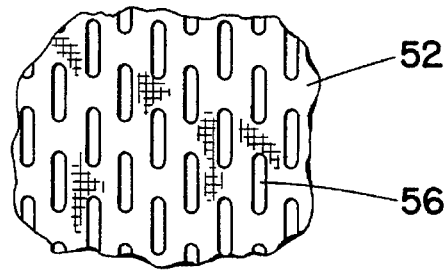
FIG. 4 is a fragmentary plan view of a stretchable layer of the dressing depicted in FIG. 1.

One suitable stretchable and flexible material that could be used to make the strip 52 is Sontara® spun-laced fabric available from DuPont. An enlarged schematic plan view of that material is shown in FIG. 4. The material includes rows of small slits 56, with the slits of one row being offset relative to the slits of an adjacent row. The presence of the slits promotes stretchability of the fabric strip.

The semi-occlusive (i.e., vapor permeable, liquid and bacteria impermeable) film 54 preferably comprises polyurethane having a thickness from 0.35 mil (mm) to 2.0 mil (0.0508 mm), most preferably 1.0 mil. Preferably, a film 54 is chosen which enables the backing sheet to exhibit an MVTR (moisture vapor transmission rate) not greater than 2,000 gm/m²/24 hrs., preferably about 1,059 gm/m²/24 hrs. It will be appreciated that the MVTR of the backing sheet 51 is a function of the moisture vapor transmission characteristics of the film 54 as well as any adhesive layers disposed on or in the backing sheet, such as the adhesion layer (if any) securing the strip 52 to the film 54. (The strip 52 is chosen to have an MVTR no less than that of the film 54.) In the event that the strip 52 is vapor permeable and liquid impermeable (rather than being vapor and liquid permeable), the vapor permeability of the strip should be at least as great as that of the film 54.

The respective outer perimeters 62, 64 of the strip 52 and film 54 are coextensive, i.e., vertically superimposed (see FIG. 1), so that the entire surface area of the strip 52 is covered by the film 54. As a result, in order for any wound vapor to escape, it must travel through the film 54. Therefore, the moisture vapor transmission rate (MVTR) through the dressing will be uniform throughout the dressing, rather than being greater in some regions than in others as in the FIG. 6 dressing. Hence, the MVTR will not vary from one size dressing to the next. In addition, the dressing can be easily handled, since the backing sheet, rather than being formed of a film as in the FIG. 5 dressing, is comprised of a laminate of a film and a non-woven fabric. Hence the dressing can be applied with greater ease and with less chance of the dressing becoming folded over and stuck to itself as compared to the FIG. 5 dressing.

The MVTR was measured by a method similar to the "Water Method" described in ASTM E 96. That is, there is provided an upright "cup" filled with water to which the test sample is affixed. The cup opening measures 60 cm. by 60 cm. Thus, a 100% relative humidity is presented to one side of the sample. The water filled cup with affixed sample is placed into a temperature controlled chamber. Unlike ASTM E 96 the chamber is not controlled to 50% relative humidity, and standard temperatures of 21°–32° C. are not used. Rather, a controlled relative humidity of 15–20% is established at a temperature of 40° C. The material is tested at the start and after 24 hrs., rather than periodically as in ASTM E 96, in order to determine the steady state of water vapor transmission rate. Thus, the MVTR measured by that test is actually the total moisture vapor transmission over a 24 hr. period.

The permanent attachment of the stretchable strip 52 to the film 54 can be effected by lamination, or by extruding the film onto the stretchable strip material. If lamination is employed, the film 54 is coated with a pressure sensitive dry adhesive, the coating being applied at a rate of 1.2–1.7 oz./yd². Regardless of whether lamination or extrusion is employed, an external side 58 of the stretchable strip 52 will adhere to an internal side 60 of the film. Hence, an external side 63 of the film will define the external face of the dressing 10. The material of the film has a lower coefficient of friction than the fabric material of the stretchable fabric strip 52, so that frictional shear forces developed upon rubbing the external face of the dressing against a surface will be lower than would be the case if the stretchable fabric strip 52 defined the external face of the dressing.

As a result, the dressing will be less likely to be rubbed off, so the strength of adhesion of the dressing to the skin can be reduced in order to lower the level of discomfort to the patient when the dressing is removed from the skin.

The coefficients of friction described herein were measured by using a Thwing Albert Model 225-1 Friction/Peel tester equipped with an integrator which averages the kinetic coefficients of friction throughout the test. During the test, the external face of the dressing was applied to a 2.5 inch square sled weighing 200 grams. The sled was moved at a constant speed of 15 cm per minute across a 100% cotton sheet and the resistance was measured in accordance with ASTM D 1894 (except for the use of a cotton sheet instead of a stainless steel test surface). Two measures are obtained by this procedure, i.e., a static friction measure and a kinetic friction measure. Preferably, the coefficient of static friction is below 1.0, and the coefficient of kinetic friction is below 0.7. Most preferably, a film 54 has been selected having a coefficient of static friction of about 0.48, and a coefficient of kinetic friction of about 0.41.

By way of comparison, a conventional spun-lace material of the type sold under the trademark Sontara® has a coefficient of static friction of 1.169 and a kinetic coefficient of 0.886 as measured by the test described above.

A polyurethane film 54 having an MVTR and coefficient of friction suitable for obtaining the characteristics set forth in this application can be obtained from Semex Medical Coated Products, 57 More Hall Rd., Frazer, Pa. 19355, under the designation KN1321-75.

If it is desired that the external face of the dressing have the "feel" of fabric, the positions of the strip 52 and film 54 could be interchanged. However, it is preferred that the external face be defined by the lower friction film 54 for reasons explained above.

The interior side 70 of the strip 52 is covered with a layer 72 of conventional medical grade adhesive, such as an acrylic. The adhesive covers substantially the entire area of that side 70. The adhesive can be laid down in a pattern in order to optimize the balance between adhesion and MVTR.

Affixed permanently to the backing sheet 52, 54 is an absorbent pad 74. An external side 76 of the pad adheres to the adhesive layer 72. The pad material preferably comprises a non-woven fabric such as an airlayered blend of rayon or polyester. The thickness and length will vary, depending upon the intended use for the dressing.

Instead of comprising a non-woven fabric, the absorbent pad 74 could comprise a hydrophilic pad partially saturated with a hydrogel, or the pad 74 could, comprise a hydrophilic foam. In either case, it might not be necessary to employ a net 80.

Figure 1:
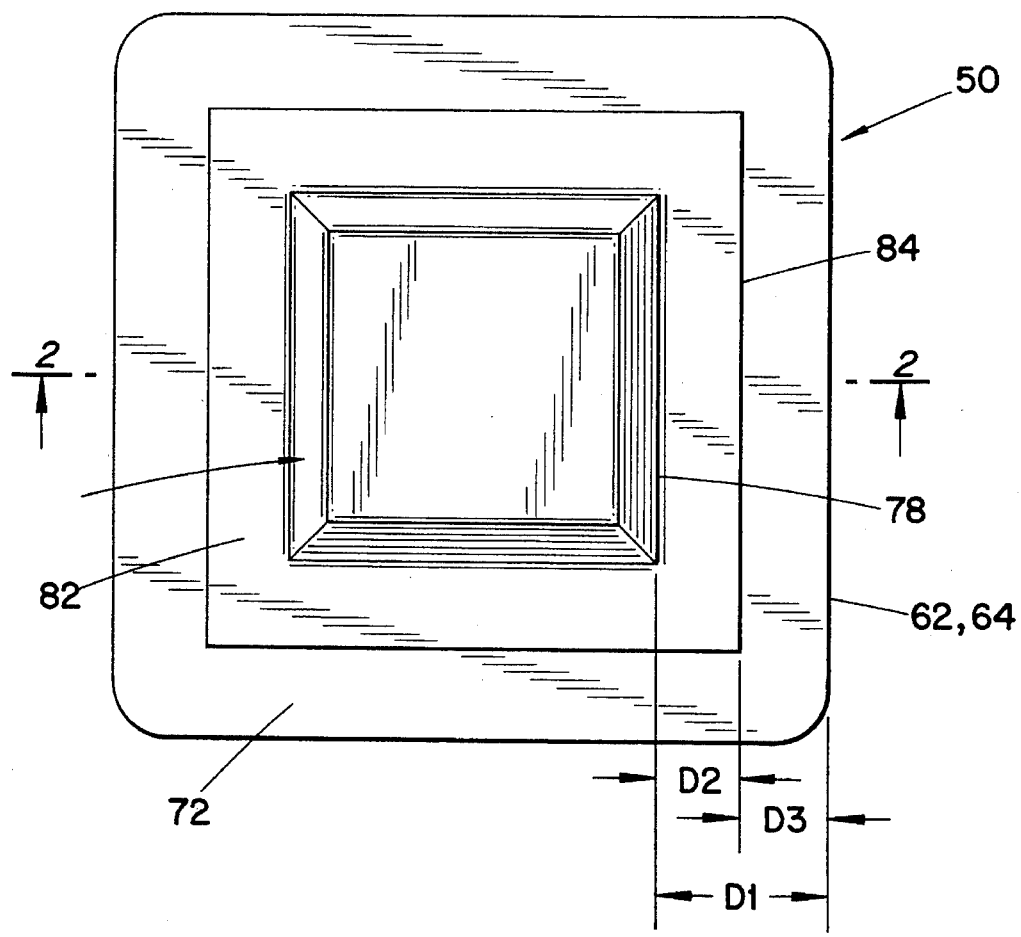
FIG. 1 is a top plan view of a wound dressing according to the present invention, with a releasable covering thereof removed.
Figure 2:
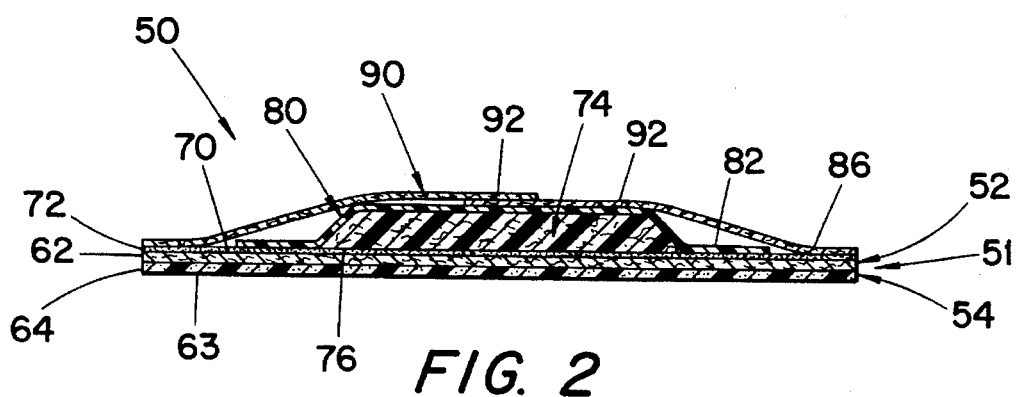
FIG. 2 is a cross sectional view taken along line 2—2 in FIG. 1, with the releasable covering being provided.

The pad 74 has a smaller surface area than the strip 52, and an outer perimeter 78 of the pad is spaced inwardly by a distance D1 from the entire outer perimeter 62 of the strip 52 (see FIG. 1). That is, no part of the pad 74 extends to the outer perimeter of the strip 52.

Overlying the pad 74 is a liquid permeable net 80 which defines a wound-contacting face of the dressing. The net material is conventional and preferably formed of a strip of polyethylene and ethylene vinyl acetate copolymer which is non-adherent to the wound. The strip 80 is perforated to allow the passage of wound moisture liquid and vapor.

A portion 82 of the net 80 is situated outwardly of the entire outer perimeter of the pad 74 and is permanently adhered to the adhesive layer 72. An outer perimeter 84 of the net is spaced outwardly from the entire outer perimeter 78 of the pad 74 by a distance D2, and is spaced inwardly from the entire outer perimeter 62 of the strip 52 by a distance D3. Hence, the entire outer perimeter 84 of the net is surrounded by a portion 86 of the adhesive layer 72. That portion 86 of the adhesive layer 72 defines a skin-attachment portion of the dressing.

Figure 3:
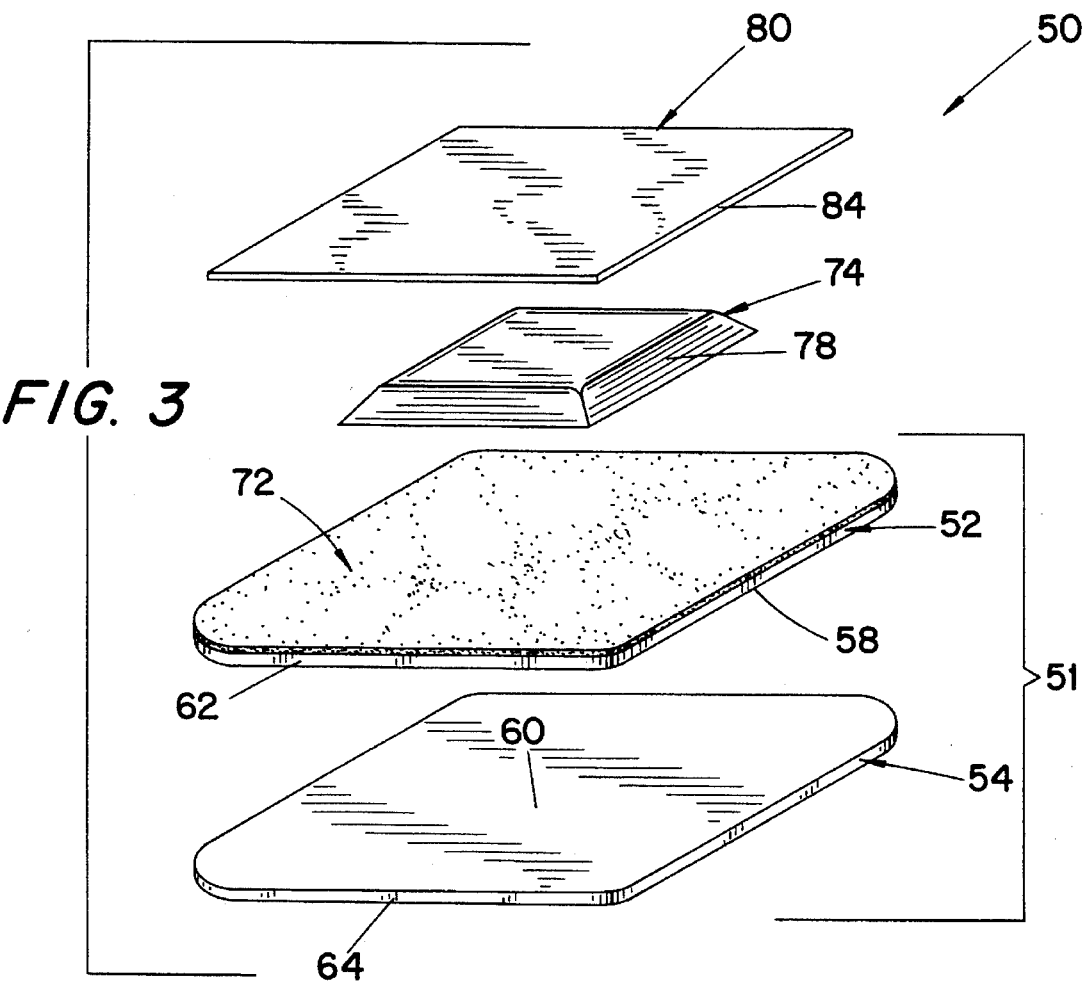
FIG. 3 is an exploded perspective view of the dressing depicted in FIG. 1.

Overlying the net 80 is a removable covering 90 defined by two overlapped sheets 92 (not shown in FIGS. 1 and 3). The sheets 92 are formed of a conventional material, e.g., paper coated with a release substance which enables the paper to be easily separated from the outer portion 86 of the adhesive layer 72.

Figure 7:
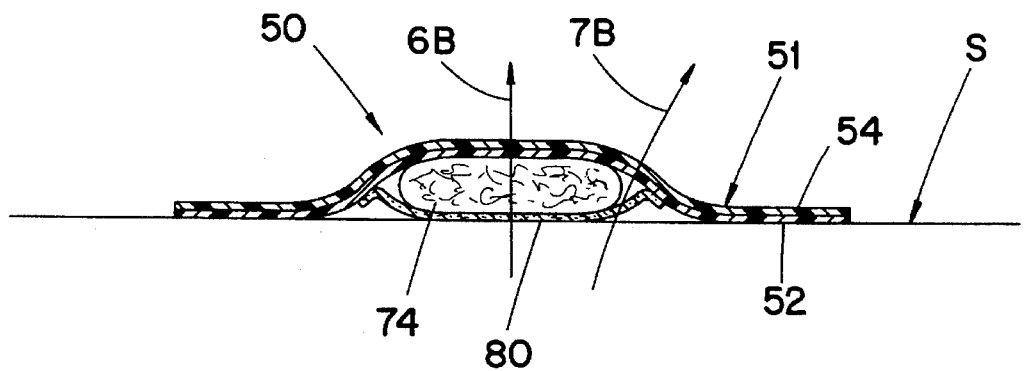
FIG. 7 is a view similar to FIG. 5 of a dressing according to the present invention adhered to a skin surface.

To apply the dressing to a wound, the user peels off the cover sheets 92, positions the net 80 against the wound and presses the outer portion 86 of the adhesive layer 72 to the skin surrounding the wound (see FIG. 7).

As the wound drains, wound exudate will pass through the net 80 and be absorbed in the pad 74. Escape of moisture vapor from the dressing can occur only through the backing sheet 51 (see arrows 6B, 7B in FIG. 7), which exhibits a uniform MVTR throughout its entire area. Therefore, the MVTR will not change from one dressing size to the next.

Furthermore, this advantage is not achieved at the expense of reduced handleability, because the backing sheet is comprised of a lamination of the film 54 and non-woven fabric 52. That lamination is much easier to manipulate and apply to the skin than in the case of the FIG. 5 dressing, for example, and possibly also in the case of the FIG. 6 dressing.

Figure 5:
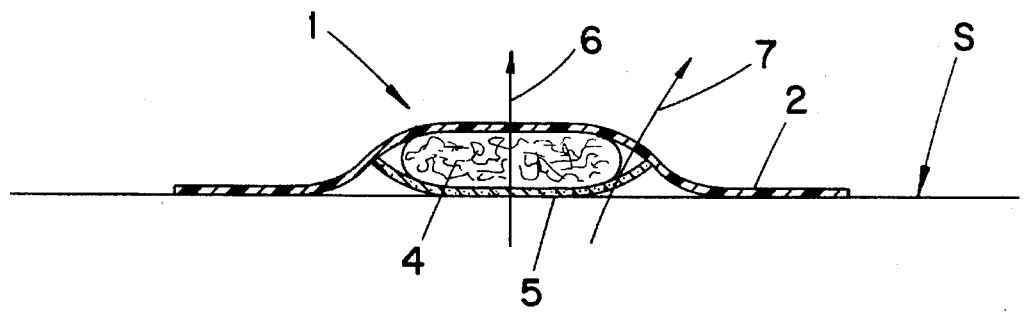
FIG. 5 is a sectional view of one prior art dressing adhered to a skin surface.
Figure 6:
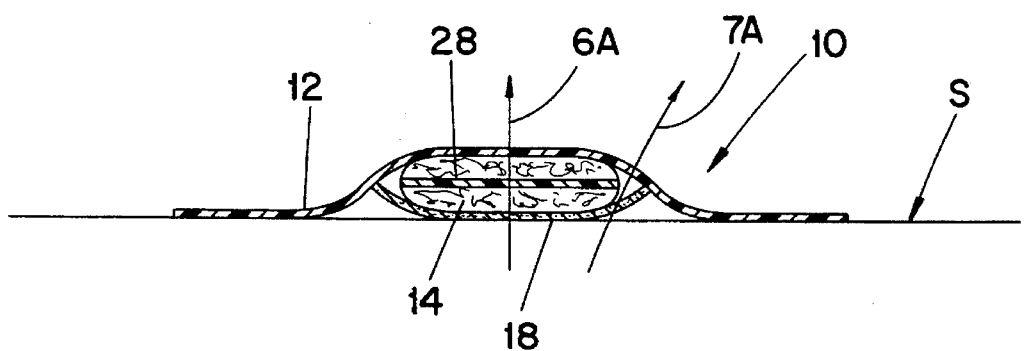
FIG. 6 is a view similar to FIG. 5 of another prior art dressing adhered to a skin surface.

Also, less frictional shear forces will be imposed on the dressing when the outer film 54 of the dressing is rubbed against a surface, as compared with the FIG. 5 dressing in which the external face of the dressing is defined by a fabric. Hence, there exists a reduced risk of wound exudate leaking from the dressing and possibly infecting others, or soiling the bedclothes.

It will be appreciated that the backing sheet, absorbent pad, and net could be of any suitable shape in addition to rectangular, e.g., round, oval, triangular, etc.

Although the present invention has been described in connection a preferred embodiment thereof, it will be appreciated by those skilled in the art that additions, deletions, modifications, and substitutions not specifically described may be made without departing from the spirit and scope of the invention as defined in the appended claims.

What is claimed is:

1. A wound dressing for promoting moist wound healing comprising:

a backing sheet formed of multiple, permanently attached layers and containing on one side a medical grade adhesive, one of said layers comprising a stretchable strip of vapor permeable, non-woven fabric, and another of said layers comprising a semi-occlusive film, said strip and said film having coextensive outer perimeters, said film disposed externally of said strip and defining an external face of the dressing, said external face exhibiting a coefficient of static friction less than 1.0 and a coefficient of kinetic friction less than 0.7; and an absorbent pad permanently mounted on said backing sheet by being affixed to said adhesive, with an outer perimeter of said pad being spaced inwardly from the entire outer perimeter of said backing sheet and from an outer perimeter of said adhesive which forms a skin-attachment portion of the dressing.

2. A wound dressing according to claim 1 further comprising a liquid permeable net overlying said pad and including an outer portion permanently affixed to said adhesive, an outer perimeter of said net being completely surrounded by a portion of said backing sheet which defines a skin-attachment portion of the dressing, said net defining a wound-contacting portion of the dressing and being formed of a material non-adherent to wounds.

3. A wound dressing according to claim 2, wherein said outer perimeter of said net is spaced outwardly from the entire outer perimeter of said pad.

4. A wound dressing according to claim 2 further including a removable covering overlying said net and releasably secured to said portion of said adhesive.

5. A wound dressing according to claim 1, wherein one side of said strip faces away from said absorbent pad, said film adhered directly to said one side of said strip.

6. A wound dressing according to claim 1, wherein said coefficient of static friction is about 0.48, and said coefficient of kinetic friction is about 0.41.

7. A wound dressing according to claim 1, wherein said strip is liquid permeable.

8. A wound dressing according to claim 1, wherein said strip and said absorbent pad are formed of synthetic materials.

9. A wound dressing according to claim 1, wherein said absorbent pad comprises a non-woven fabric.

10. A wound dressing according to claim 1, wherein said absorbent pad comprises a hydrophilic material partially saturated with a hydrogel.

11. A wound dressing according to claim 1, wherein said absorbent pad comprises a hydrophilic foam.

12. A wound dressing according to claim 1, wherein said backing sheet has an MVTR of about 1,059 to 2,000 gm/m$^2$/24 hrs.

13. A wound dressing for promoting moist wound healing comprising:
   a backing sheet including:
      a stretchable, vapor permeable, non-woven fabric strip having internal and external sides, and
      a semi-occlusive film having internal and external sides, said internal side of said film permanently adhered to said external side of said strip such that said external side of said film defines an external face of the dressing, said external face exhibiting a coefficient of static friction less than 1.0, and a coefficient of kinetic friction less than 0.7, said film having an outer perimeter which is substantially coextensive with an outer perimeter of said strip;
   a pressure-sensitive adhesive disposed on said interior side of said strip;
   an absorbent pad having internal and external sides, said external side of said pad permanently adhered to said adhesive, said pad having an outer perimeter spaced inwardly from the entire outer perimeter of said strip; and
   a liquid permeable net overlying the entire interior side of said pad to define a wound-contacting face of the dressing, a portion of said net situated outwardly of the entire outer perimeter of said pad and permanently adhered to said adhesive, said net having an outer perimeter spaced outwardly from the entire outer perimeter of said pad and spaced inwardly from the entire outer perimeter of said strip such that said entire outer perimeter of said net is surrounded by a portion of said adhesive which defines a skin attachment portion of the dressing, said net formed of a material non-adherent to wounds.

14. A wound dressing according to claim 13, wherein said coefficient of static friction of said external face is about 0.48, and said coefficient of kinetic friction of said external face is about 0.41.

15. A wound dressing according to claim 13, wherein said backing sheet has an MVTR of about 1059 gm/m$^2$/24 hrs.

16. A wound dressing for promoting moist wound healing comprising:
   a backing sheet formed of multiple, permanently attached layers and containing on one side a medical grade adhesive, one of said layers comprising a stretchable strip of vapor permeable, non-woven fabric, and another of said layers comprising a semi-occlusive film, said strip and said film having coextensive outer perimeters, said film disposed externally of said strip and defining an external face of the dressing; said backing sheet having an MVTR from about 1,059 to 2,000 gm/m$^2$/24 hrs; and
   an absorbent pad permanently mounted on said backing sheet by being affixed to said adhesive, with an outer perimeter of said pad being spaced inwardly from the entire outer perimeter of said backing sheet and from an outer perimeter of said adhesive which forms a skin-attachment portion of the dressing.

17. A wound dressing according to claim 16, wherein said backing sheet has an MVTR of about 1,059 gm/m$^2$/24 hrs.

* * * * *